United States Patent [19]

Willingham et al.

[11] Patent Number: 5,037,989

[45] Date of Patent: Aug. 6, 1991

[54] PHENOXYALKANOL AS A STABILIZER FOR ISOTHIAZOLONE CONCENTRATES

[75] Inventors: Gary L. Willingham, Glenside; John R. Mattox, Perkasie, both of Pa.

[73] Assignee: Rohm and Haas Company, Philadelphia, Pa.

[21] Appl. No.: 505,201

[22] Filed: Apr. 5, 1990

[51] Int. Cl.$^5$ .................... C07D 91/10; C07D 275/02
[52] U.S. Cl. .................................................. 548/213
[58] Field of Search ......................... 548/213; 514/372

[56] References Cited

PUBLICATIONS

Izutsuya, Chemical Abstracts vol. 108:17783d 1987.

Primary Examiner—Mukund J. Shah
Assistant Examiner—Matthew V. Grumbling
Attorney, Agent, or Firm—Michael B. Fein

[57] ABSTRACT

Phenoxyalkanols are used to stabilize isothiazolone concentrates.

14 Claims, No Drawings

PHENOXYALKANOL AS A STABILIZER FOR ISOTHIAZOLONE CONCENTRATES

BACKGROUND OF THE INVENTION

1. Field of the Invention

This invention relates to stable compositions of 3-isothiazolones, their preparation, and their use in controlling living organisms.

2. Description of the Prior Art

German patent no. 3508928 Guilini Chemie, claims a methylparaben, propylparaben and propylene glycol containing composition for antimicrobial and antioxidative stabilization of cosmetics, which contains a list of compounds including optionally isothiazolone and also optionally 2-phenoxyethanol. See also European Patent Application 194466 which is substantially the same as the aforementioned German Patent.

Until now typical means for stabilization of isothiazolones against thermal degradation or storage degradation has generally been by metal salts, formaldehyde or formaldehyde releasers, and other stabilizers suggested in, for example, U.S. Pat. No. 4,906,274.

Both formaldehyde or formaldehyde-releasers and salt stabilization of isothiazolones have some drawbacks. In certain applications it is desirable to avoid addition of certain stabilizers by virtue of their volatility, decomposition under high heat, higher cost, difficulty in handling, potential toxicity, and the like

SUMMARY OF THE INVENTION

This invention comprises a composition which contains from about 0.1 to about 99.9 parts of one or more isothiazolones and an amount of a phenoxyalkanol sufficient to stabilize the isothiazolone concentrate.

DETAILED DESCRIPTION OF THE INVENTION AND THE PREFERRED EMBODIMENTS

The 3-isothiazolones of interest include those disclosed in U.S. Pat. Nos. 3,523,121 and 3,761,488 as represented by the following formula:

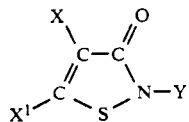

wherein Y is hydrogen; an alkyl or substituted alkyl of 1 to 18 carbon atoms, preferably from 4 to 10 carbon atoms; an unsubstituted or halogen substituted alkenyl or alkynyl of 2 to 8 carbon atoms, preferably from 2 to 4 carbon atoms; a cycloalkyl or substituted cycloalkyl of 3 to 12 carbon atoms, preferably from 5 to 8 carbon atoms; an aralkyl or halogen-, lower alkyl-, or lower alkoxy-substituted aralkyl of up to 10 carbon atoms; or an aryl or halogen-, lower alkyl-, or lower alkoxy-substituted aryl of up to 10 carbon atoms; and X and $X^1$ are hydrogen, halogen, or a ($C_1$–$C_4$)alkyl.

Representative Y substituents include methyl, ethyl, propyl, isopropyl, butyl, hexyl, octyl, cyclohexyl, benzyl, 3,4-dichlorophenyl, 4-methoxybenzyl, 4-chlorobenzyl, 4-methoxyphenyl, 4-chlorophenyl, phenethyl, 2-(4-chlorophenyl)ethyl, hydroxymethyl, chloromethyl, chloropropyl, hydrogen, and the like.

Where the expression "lower" is employed in conjunction with terms, such as alkyl, alkoxy, etc., it is intended to indicate that the alkyl or alkyl portion thereof has 1 to 4 carbon atoms, i.e., ($C_1$–$C_4$).

By a substituted alkyl group is meant an alkyl group having one or more of its hydrogen atoms replaced by another substituted group. Examples of the substituted alkyl groups with characterize 3-isothiaozlones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituent aralkyl groups which characterize 3-isothiaozlones of this invention include halogen-, lower alkyl-, or lower alkoxy-substituted aralkyl groups, and the like.

By a substituted aryl group is meant an aryl group, such as benzene, naphthalene, or pyridine, having one or more of the hydrogen atoms on the aryl ring replaced by another substitutent group. Examples of such substitutent groups include halogen, nitro, lower alkyl, lower alkyl-acylamino, lower carbalkoxy, sulfamyl, and the like.

Preferred isothiazolones are 5-chloro-2-methyl-3-isothiazolone, 2-methyl-3-isothiazolone, 2-octyl-3-isothiazolone, 4,5 dichloro-2-cyclohexyl-3-isothiazolone and 4,5-dichloro-2-octyl-3-isothiazolone.

For certain uses, such as shipping of large quantities, more concentrated solutions may also be utilized.

The resultant solution comprises up to about 25% by weight adjuvant selected from the group consisting of surfactant, inorganic salt, polymeric dispersant, humectant, viscosity modifier, and freezing point depressant.

Preferably the concentrate contains little or no water, preferably less than about 5% by weight water.

The isothiazolone may be present in a bulk form or packaged or encapsulated in some manner, including a form for controlled release. The ratio of isothiazolone to phenoxyalkanol is preferably from about 0.1:99.9 to about 25:75.

Suitable phenoxyalkanols are phenoxyethanol and phenoxyisopropanol.

This invention permits the stabilization of isothiazolones wherein the previously necessary stabilization salts are substantially reduced and even eliminated.

Uses of these new organically stabilized biocides are typically at any locus subject to contamination by bacteria, fungi or algae. Typical loci are aqueous systems such as water cooling, laundry rinse water, oil systems such as cutting oils, oil fields and the like where microorganisms need to be killed or where their growth needs to be controlled.

The stabilized biocide compositions of this invention containing reduced levels of salt or no salt are advantageous over salt stabilized isothiazolones described in the art and are the biocides of choice where salts pose a problem. For example, certain emulsions upon the addition of a salt may coagulate. The compositions of this invention avoid this problem and therefore can be used in emulsions such as photographic emulsions, coating emulsions, (e.g. paints) to form solid protective or decorative films; electronic circuitry, wood, metals, plastics, fibers, membranes, carpet backings, ceramics and the like where surfaces need to be coated or protected, adhesives, caulks, and sensitive emulsions.

The salt free compositions of this invention are useful in fuel systems such as diesel fuel, gasoline, kerosene, certain alcohols, and the like, because they eliminate the possibility of salt deposits on component parts. Another reason for eliminating salts is to avoid an environment in which corrosion can occur. For example, chloride salts (among others) have a corrosive effect on many metals and are to be avoided where possible. In water treatment systems where low cation and anion levels are important, this is especially true. Those familiar with the art in various areas where biological growth needs to be controlled will quickly recognize those applications where significant reduction of or elimination of salts will be desired. In many cases it is necessary to eliminate interactions between the stabilizing salts and other components of the system or formulation components which otherwise could reduce the performance or value of such systems.

Because isothiazolone biocides are so active, the low level required to achieve stabilization also makes them ideal when compared to many known biocides because at the low levels required they are not likely to interfere with other components in systems requiring protection or with systems upon which the protected systems will be applied.

Potential areas of general application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and many other applications where water and organic materials come in contact under conditions which allow the growth of undesired microorganisms.

In some cosmetic formulations, it is also important to have low water and salt content. Eliminating nitrate salts avoids the possibility of nitrosamine formation with any amines present in the formulation. Removal or reduction of multivalent cations from the biocide may also eliminate the known possibility of creating physical incompatibility problems in certain cosmetic formulations caused by precipitation of salts or complexes.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

Isothiazolones are used in oil field water treatment, as watercooling system microbiocides, as preservatives for aqueous dispersions or organic polymers, as wood pulp white water slimicides, as cosmetic preservatives, as cutting oil, jet fuel, and heating oil preservatives, and the like. Solutions of isothiazolones are also applied to a solid substrate, such as fabric, leather, or wood, as a preservative, or admixed with plastics.

The products of this invention are especially useful as preservatives for the following:

1. Cosmetics, as it eliminates or substantially reduces the presence of nitrates which under certain conditions in the presence of amines or amine precursors may lead to the formation of nitrosoamines.

2. Oils and fuels, since added salts and moisture are eliminated or minimized thus preventing potential corrosion, deposition or sludge formation.

3. Emulsions and dispersions that are sensitive to divalent cations are those contained in a wide variety of products, such as paints, cosmetics, floor polishes and binders.

4. Plastics, as it eliminates or substantially reduces precipitated salts which can contribute directly or indirectly to haze, opacity, or physical weakness in the surface.

The following example will further illustrate this invention, but is not intended to limit it in any way. All parts and percentages are by weight and all temperatures in degrees Centigrade, unless otherwise stated.

For comparison of the stabilization of the compositions of this invention with known materials the following tests were employed: using temperature-controlled ovens, vials of solvent, and isothiazolone were made up and heated for fixed periods of time. The percentage of the starting isothiazolone remaining was determined by high performance liquid chromatography (HPLC). A temperature of 55° C. was used. Results were considered indicative of acceptable stability when remainder values indicated essentially no loss during the time specified for the isothiazolone or isothiazolone mixture studied.

I. Stability Test for
5-Chloro-2-methyl-3-isothiazolone/2-Methyl-3-isothiazolone

EXAMPLE 1

A 15% by weight solution of 5-chloro-2-methyl-3-isothiazolone/2-methyl-3-isothiazolone (4.3/1:wt/wt) was prepared in phenoxyethanol and in dipropylene glycol. The solutions were stored at 55° C. and analyzed for total isothiazolone (AI) remaining after 1 and 2 weeks. Results are give in Table 1.

TABLE 1

| STABILIZATION OF 5-CHLORO-2-METHYL-3-ISO-THIAZOLONE/2-METHYL-3-ISOTHIAZOLONE BY PHENOXYETHANOL AT 55° C. | | |
|---|---|---|
| Solvent | 1 week | 2 weeks |
| Dipropylene Glycol | 89 | 2 |
| Phenoxyethanol | 95 | 97 |

We claim:

1. A method of stabilizing a 3-isothiazolone against chemical decomposition comprising dissolving said 3-isothiazolone in a sufficient amount of phenoxyalkanol to stabilize the isothiazolone against chemical decomposition.

2. Method of claim 1 wherein the weight ratio of 3-isothiazolone to phenoxyalkanol is about 0.1:99.9 to about 25:75.

3. Method of claim 1 wherein the resultant solution further comprises up to about 25% by weight adjuvant selected from the group consisting of surfactant, inorganic salt, polymeric dispersant, humectant, viscosity modifier, and freezing point depressant.

4. Method of claim 1 wherein said 3-isothiazolone is selected from the group consisting of 5-chloro-2-methyl-3-isothiazolone, 2-methyl-3-isothiazolone, 2-octyl-3-isothiazolone, 4,5-dichloro-2-cyclohexyl-3-isothiazolone and 4,5-dichloro-2-octyl-3-isothiazolone.

5. Method of claim 1 wherein the resulting solution comprises less than about 5% by weight water.

6. Method of claim 5 wherein said solution contains no water.

7. Method of claim 1 wherein said phenoxyalkanol is selected from the group consisting of phenoxyethanol and phenoxyisopropanol.

8. Composition comprising a 3-isothiazolone compound and sufficient amount of phenoxyalkanol to stabilize said isothiazolone against chemical decomposition.

9. Composition according to claim 8 wherein said phenoxyalkanol is present a weight ratio of 3-isothiazolone to phenoxyalkanol of about 0.1:99.9 to about 25:75.

10. Composition according to claim 8 wherein said composition further comprises up to about 25% by weight adjuvant selected from the group consisting of surfactant, inorganic salt, polymeric dispersant, humectant, viscosity modifier, and freezing point depressant.

11. Composition according to claim 8 wherein said 3-isothiazolone is selected from the group consisting of 5-chloro-2-methyl-3-isothiazolone, 2-octyl-3-isothiazolone, 4,5-dichloro-2-cyclohexyl-3-isothiazolone and 4,5-dichloro-2-octyl-3-isothiazolone.

12. Composition according to claim 8 comprising less than about 5% by weight water.

13. Composition according to claim 8 containing no water.

14. Composition according to claim 8 wherein said phenoxyalkanol is selected from the group sonsisting of phenoxyalkanol and phenoxyisopropanol.

* * * * *